United States Patent [19]

Freedland

[11] Patent Number: 5,098,433
[45] Date of Patent: Mar. 24, 1992

[54] WINGED COMPRESSION BOLT ORTHOPEDIC FASTENER

[76] Inventor: Yosef Freedland, 107 N. Poinsettia Pl., Los Angeles, Calif. 90036

[21] Appl. No.: 336,721

[22] Filed: Apr. 12, 1989

[51] Int. Cl.$^5$ .............................................. A61B 17/58
[52] U.S. Cl. ........................................ 606/63; 606/60; 606/62; 606/68
[58] Field of Search .......... 128/92 Y, 92 YZ, 92 YY, 128/92 YK, 92 YW, 92 YV, 92 YT, 92 YS; 606/63, 60, 62, 68

[56] References Cited

U.S. PATENT DOCUMENTS

| | | | |
|---|---|---|---|
| 624,969 | 5/1899 | Peterson | 128/92 YF |
| 2,077,804 | 4/1937 | Morrison | 128/92 YW |
| 4,091,806 | 5/1978 | Aginsky | 128/92 YY |
| 4,409,974 | 10/1983 | Freedland | 128/92 |
| 4,453,539 | 6/1984 | Raftopoulos et al. | 128/92 YY |
| 4,519,100 | 5/1985 | Wills et al. | 128/92 YW X |
| 4,590,930 | 5/1986 | Kurth et al. | 128/92 YY |
| 4,632,101 | 12/1986 | Freedland | 128/92 YY |
| 4,721,103 | 1/1988 | Freedland | 128/92 YY |

FOREIGN PATENT DOCUMENTS

| | | | |
|---|---|---|---|
| 165666 | 12/1985 | European Pat. Off. | 128/87 R |
| 1049055 | 10/1983 | U.S.S.R. | 128/92 YY |
| 1055498 | 11/1983 | U.S.S.R. | 128/92 YW |
| 1338852 | 9/1987 | U.S.S.R. | 128/92 YY |

*Primary Examiner*—Robert A. Hafer
*Assistant Examiner*—Kevin G. Rooney

[57] ABSTRACT

A winged compression bolt for repairing or fusing bone which is implanted and later removed from bone through a single skin incision. The device includes a central elongated shaft which movably sits in an outer cylindrical tube and supports adjacent one of its ends a pair of wings. A bore is drilled through the bone portions, the device is inserted and the wings are rotated to the horizontal position and compressed against the edge of the outer cylindrical tube and an adjacent bone surface. A securing means is on the opposite end of the central elongated shaft and tightened against the adjacent edge of the outer cylindrical tube and an adjacent bone surface, compressing the bone portions between the securing means and the wings.

To remove the device, the securing means is removed, the outer cylindrical tube is removed and the central elongated shaft is pulled through the bore in the bone, causing the wings to rotate from the horizontal to the vertical position and trail the shaft as it is removed from the bore.

34 Claims, 4 Drawing Sheets

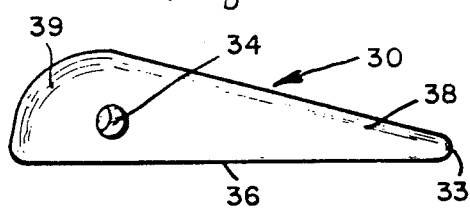
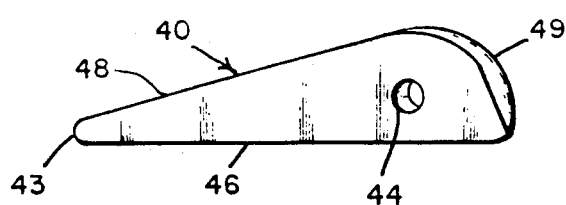
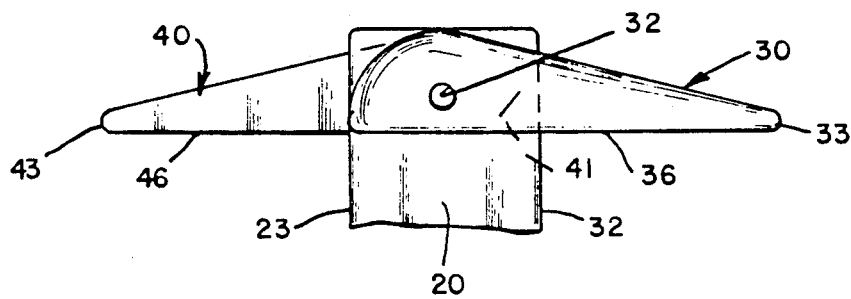
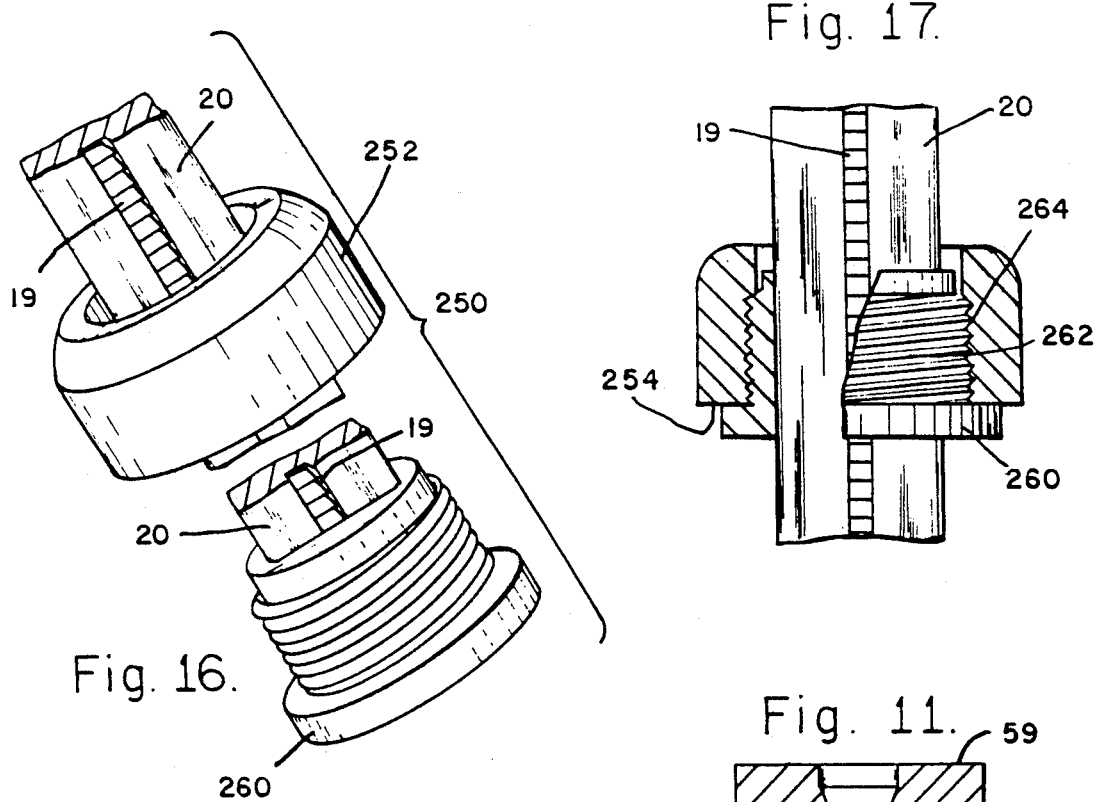
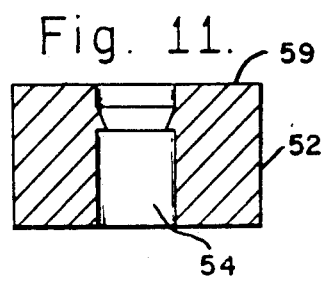

Fig. 13.
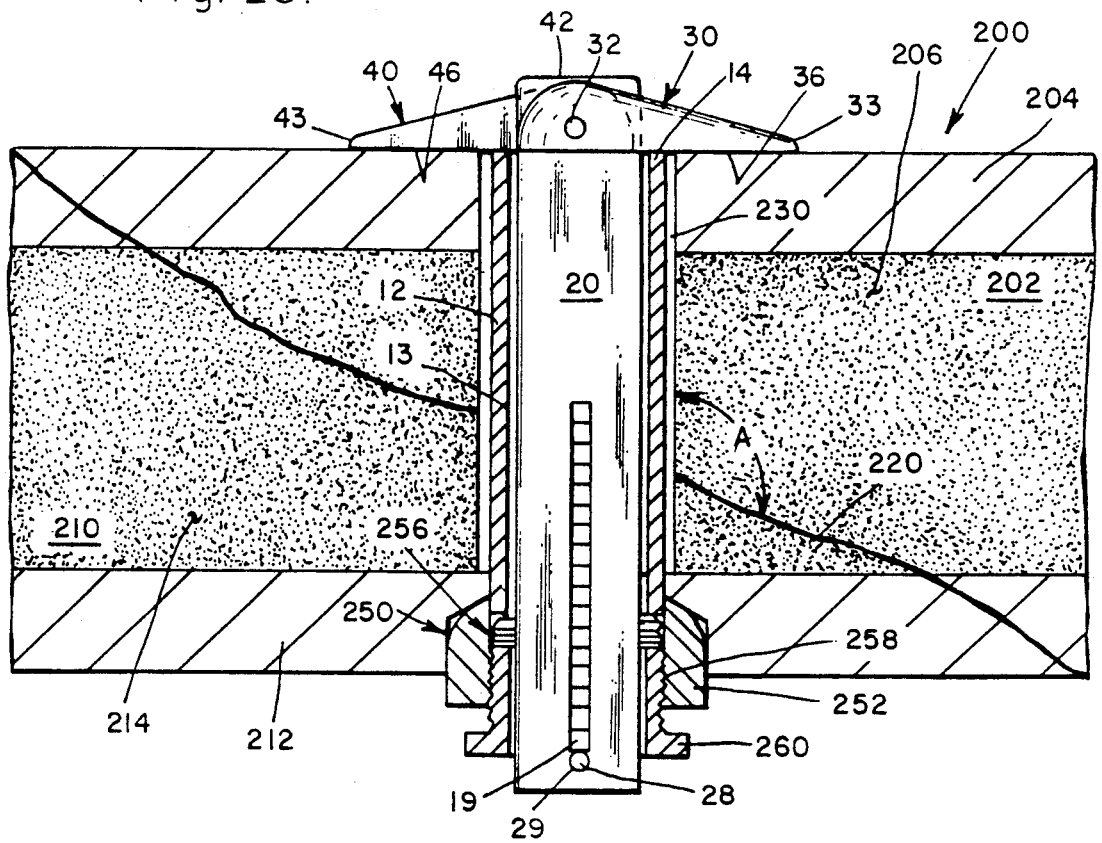
Fig. 14.
Fig. 15.
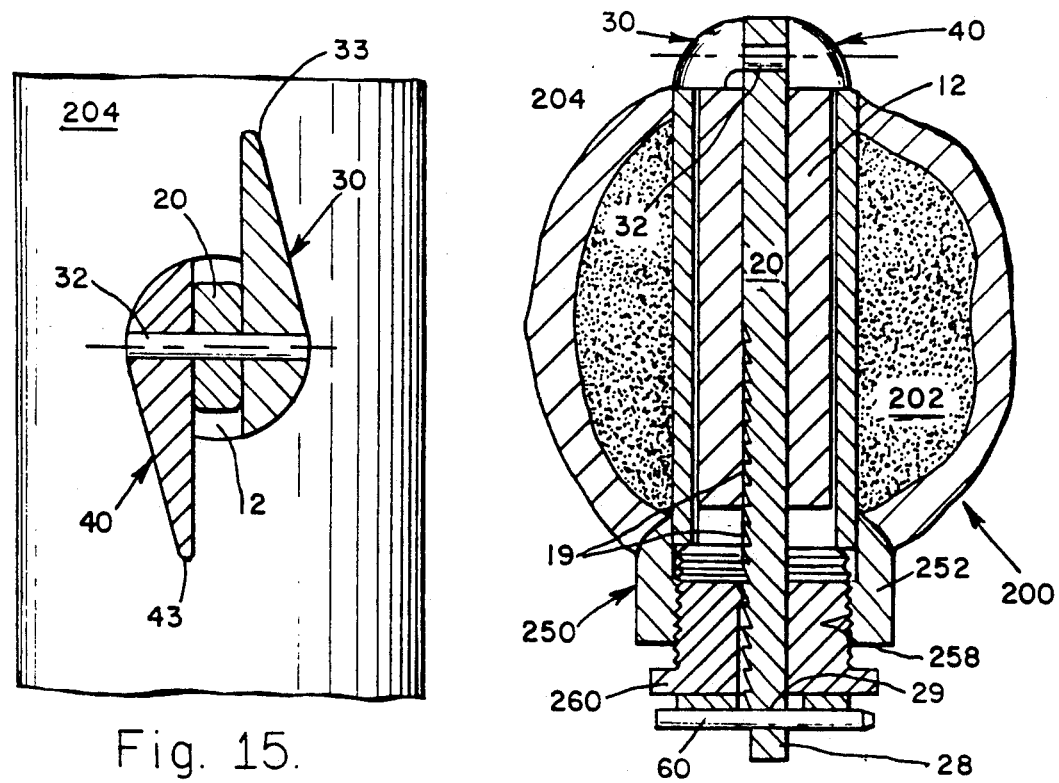

WINGED COMPRESSION BOLT ORTHOPEDIC FASTENER

BACKGROUND OF THE INVENTION

1. Field of the Invention

The present invention relates to surgical fastening devices used particularly in the field of orthopedic surgery for fusing two bones relative to each other and fixating portions of a broken bone together under compressive force. The present invention further relates to surgical implant devices utilized in procedures where rigid internal fixation in the fusion of two bones relative to each other and fixation of bone portions is desired.

2. Description of the Prior Art

Various orthopedic pins and fasteners have been devised to aid in properly compressing bones or portions of a fractured bone together so as to promote as much as possible their prompt fusion and primary healing. The most common internal fixation devices used to aid in the fusion of bones or fixation of a fractured bone include and rely upon screw fasteners which must be entered and advanced into the bone structures worked upon.

Internal fusion and fixation devices limit the motion between bones as do externally placed rods and bolts. The internal fusion and fixation devices though, allow earlier mobilization of the affected body part, more precise placement of fixation or fusion devices and reduces chance for infection entry through contamination from the external communication of fixation/fusion devices. Present-day techniques for Internal Fusion or Fixation of bones which employ the use of screws require a variety of lengths and diameters of screws which may be used alone or in conjunction with various plates, washers or wires. Screws fixate two pieces of fractured bone together by the compressive forces created through the shear of the screw threads embedded in the hard cortical bone and the compression of the head of the screw against the opposite surface of the bone. In fusing two adjacent bones, the screw threads anchor usually in softer cancellous bone. In fusing two bones or fixating portions of single bone, the threads anchor along the bore in the bone and resist displacement by the bone's intrinsic shear strength. Prior to inserting the screw, the surgeon must drill a bore through the bone and "tap" threads in the bore. After insertion of the screw, should the forces generated at the screw site be greater than the intrinsic strength of the "shear cylinder", the screw(s) may either explosively strip the thread from the bore or gradually loosen during the fixation period, failing to achieve the proper anchoring of the bone and accruing loss of compressive force. This is particularly evident in soft cancellous bone fusion where shear cylinder strength is very low.

Another group of devices which are primarily designed for use in tubular bones such as femur or tibia provide elongate fasteners which are of relatively narrow configuration when inserted into bone being worked upon and which operate to expand laterally or radially after being inserted to attain fixation in the bone. These devices are commonly classified or called "expanding nail devices". One such device is disclosed in my prior U.S. Pat. No. 4,409,974 for Bone-Fixating Surgical Implant Device issued in 1983.

Another group of devices as illustrated in my issued U.S. Pat. No. 4,632,101 entitled "Orthopedic Fastener" involves a surgical implant device for fixating bones and bone portions. The device is an elongate generally cylindrical unit surgically implanted within living bone portions, and includes a plurality of pivotally mounted struts which are deployed within the soft cancellous material of the bone distant from the fractured portion thereof. The struts are pivotally deployed radially outward from the unit until achieving an oblique angle and anchoring contact with the interior surface of the surrounding hard cortex of the distant portion of the fractured bone is established.

The expanding nail type devices discussed above are implant devices characterized by a tubular member having a plurality of triangular shaped arms. The implant device is inserted into a bore in the bone worked upon, across the fixation site, with the arms in a radially folded or collapsed position. Once inserted, the arms are caused to extend radially outward and are anchored against the cancellous material in the bone. The invention in my U.S. Pat. No. 4,632,101 is an improvement in this apparatus and also operates on the principle that the compressive force to hold the bone portions together is generated by inserting the device within the bone and the arms or struts are deployed within the bone to form anchors within the bone. Neither the expanding nail type devices or my Orthopedic Fastener provide an apparatus which have rotatable wings which lie beyond the end of the hollow cylinder.

SUMMARY OF THE PRESENT INVENTION

The present invention is a surgical implant device for fusing bones or fixating fractured portions of a single bone in a living body by providing a compressive and stabilizing force. The device includes a central elongated shaft which supports a pair of oppositely deposed wings which is inserted into the bone portions while circumferenced by a cylindrical tube. These wings when opened against compact bone and compressed against the bone surface through an outer securing means located adjacent the opposite end of the central elongate shaft, provide a compressive force to fuse the bones or fixate portions of a bone together with a compressive force. The present invention is therefore a winged compression bolt which is a fusion and fixation device that relies on the compressive forces generated between the wings and the securing means of the bolt. Both the securing means of the winged compression bolt and the wings of the bolt lie on, within, or in close proximity to hard cortical bone surfaces. As the securing means is tightened, the two ends compress the interfacing surfaces of the bones or portions of a single bone together.

The preferred use of the present invention is to fuse two bones together. The present invention may also be used to fixate two sections of broken bone together. In this application, the present invention is a surgical implant device for fixating bone and bone portions in a living body by providing a compressive force external to bone surfaces to hold the broken sections of bone together. In either case the device is the same and includes an outer cylindrical tube or sleeve and a central elongated shaft which can be movably inserted into the outer cylindrical tube, and which supports thereon adjacent one of its ends a pair of oppositely disposed wings which can be opened on one face of bone and compressed against the wall of the outer cylindrical tube and against an adjacent face of bone through an outer securing means located adjacent the opposite end of the central elongate shaft, to thereby provide a compressive force to fixate or fuse the broken sections of bone or bones together from a compressive force generated against the cortical surface of the bone or bones. In this embodiment, the present invention is therefore a winged compression bolt which is a fixation and fusing device that relies on the compressive forces generated between the wings and the securing means of the bolt. Both the securing means of the winged compression bolt and the wings of the bolt lie on the surface of compact bone. As the bolt is tightened, the two ends compress the surfaces of the bone together.

In its preferred embodiment as a fusion device, it has been discovered, according to the present invention, that if the source of fusion of two sections of bone is generated from a compressive force as opposed to shear force of a screw, the potential pullout strength of the device and hence the fusing force is much stronger and healing will be promoted faster since both cortical and cancellous bone strength is greatest in compression and weakest in shear. Shear is the force utilized to resist displacement.

It has further been discovered, according to the present invention as a fusion device, that the apparatus of a winged compression device permits easy insertion of the apparatus in a pre-drilled bore in the bone portion and does not require tapping. This embodiment further is easily deployed and tightened and can be removed easily after long periods of implantation in the bone.

It has additionally been discovered, according to the present invention as a fusion device, that the apparatus of the winged compression device can be utilized in situations in which a screw thread has either already stripped the bone or could be expected to strip the bore in the bone of its threads due to the high stress at the fusion site verses the screw pullout force.

It has also been discovered, according to the present invention as a fusion device, that the use of the winged compression device does not need to withstand torquing forces as a screw does during its insertion. Whereas a screw needs rigidity and great torque strength of its central shaft, the shaft of the present invention winged compression bolt primarily needs to withstand only compression and/or tensile forces during and following its insertion. This could allow a greater variety of flexible materials with primarily high tensile strengths from which it could be manufactured.

It has further been discovered, according to the present invention as a fusion device, that use of spread wings to generate a portion of the fusion or compressive force against the exterior or interior of hard cortex of the bone spreads the source of fusion or compression over a harder substance than cancellous bone screws.

In its alternative embodiment as a fixation device between bone portions of a single bone, it has been discovered, according to the present invention, that if the source of fixation of two broken sections of bone is generated from a compressive force, the fixation is much stronger and healing will be promoted faster since bone strength is greatest in compression and weakest in shear.

It has further been discovered, according to the present invention as a fixation device, that the use of an external smooth surface cylinder in which to house the shaft carrying the wings and securing means permits easy insertion of the apparatus in a pre-drilled bore in the bone. This embodiment further is easily deployed and tightened and can be removed easily after long periods of implantation in the bone.

It has additionally been discovered, according to the present invention as a fixation device, that the apparatus of the external cylinder and internal shaft can be utilized in situations in which a screw thread has either already stripped the bone or could be expected to strip the bore on the bone of its threads due to the high stress at the fixation site and the low strength of the bone's shear.

It has also been discovered, according to the present invention as a fixation device, that the use of the external cylinder and internal shaft supporting the compression creating apparatus does not need to withstand torquing forces as a screw does during its insertion. Whereas a screw needs rigidity and great torque strength of its central shaft, the shaft of the present invention winged compression bolt primarily needs to withstand only tensile forces following its insertion. This could allow a greater variety of tensile materials with primarily high tensile strengths from which it could be manufactured.

It has further been discovered, according to the present invention as a fixation device, that use of spread wings to generate a portion of the compressive force against the hard cortex of the bone spreads the source of compression over a wider area than a screw and thereby reduces the possibility of shattering a portion of bone through the compressive forces.

It is therefore an object of the present invention to provide a fusion apparatus which can be easily inserted through bore portions and provide a compressive force against the interior or exterior cortex of a bone and the external cortex of an adjacent bone.

It is another object of the present invention as a fusion apparatus to eliminate the necessity of creating a threaded bore through the two bones and fastening the two bones together through a screw means.

It is another object of the present invention as a fusion apparatus to eliminate the generation of binding forces for fusing bones together through utilization of the soft cancellous portion of the bone and instead to generate the compressive forces from the hard cortex of the bones.

It is a further object of the present invention as a fusion device to provide an apparatus with a minimum of moving parts and which can create a compressive force fusing two bones together, to thereby provide for easy and efficient insertion of the apparatus through the section of the two bones and subsequent easy and efficient removal after the sections of bone have healed.

It is therefore an object of the alternative fixation embodiment of the present invention to provide an apparatus which can be easily inserted through sections of broken bone and provide a compressive force against the cortical faces of the bone.

It is another object of the present invention as a fixation apparatus to eliminate the necessity of creating a threaded bore within the sections of broken bone and fastening the sections together through a screw means.

It is an additional object of the present invention to provide an apparatus as a fixation device which eliminates the necessity of placing objects into the bones and creating a source of compression from within a shear cylinder of the bone as opposed to against the surfaces of the sections of bone, to provide the mechanism for fastening the bone sections together.

It is another object of the present invention to eliminate the generation of binding forces for fixating sections of broken bone together through utilization of the cancellous portion of the bone and instead to generate the compressive forces from the hard outer cortex of the bone.

It is a further object of the present invention as a fixation device to provide an apparatus with a minimum of moving parts and which can create a compressive force fixating two sections of bones together, to thereby provide for easy and efficient insertion of the apparatus through the bones and subsequent easy and efficient removal after the bones have healed.

It is an additional object of the present invention as a fixation device to provide an apparatus which spreads the compressive force over an area of bone as opposed to a small local section of a shear cylinder of bone, to thereby create less stress at one local area and reduce the possibility of shattering a portion of bone.

Further novel features and other objects of the present invention will become apparent from the following detailed description, discussion and the appended claims, taken in conjunction with the drawings.

DRAWING SUMMARY

Referring particularly to the drawings for the purpose of illustration only and not limitation, there is illustrated:

FIG. 4 is a front elevational view of first wing 30.

FIG. 5 is a front elevational view of second wing 40.

FIG. 6 is a front elevational view of the upper portion of shaft 20 with wings 30 and 40 in the fully opened position.

Figure 7:
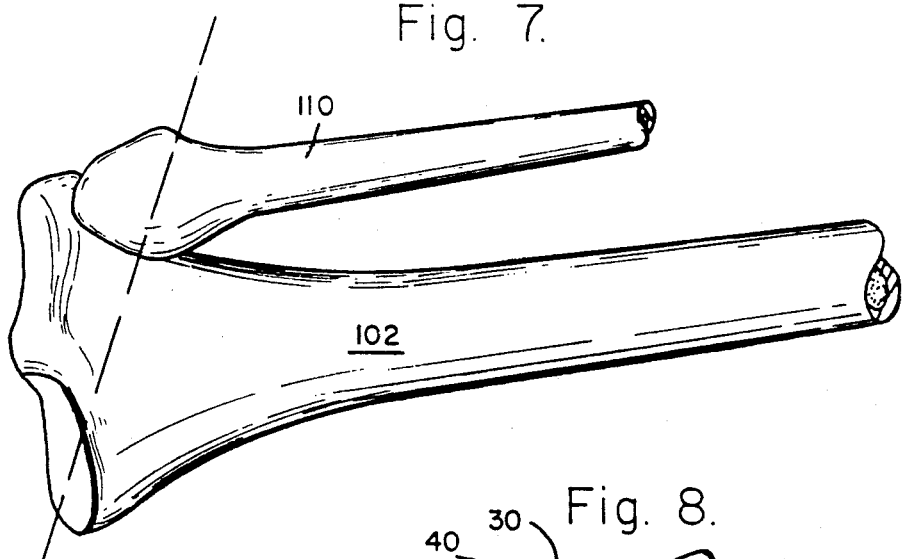

FIG. 7 is a perspective view of the placement of two bones relative to one another prior to the implantation of the present invention winged compression bolt.

Figure 8:
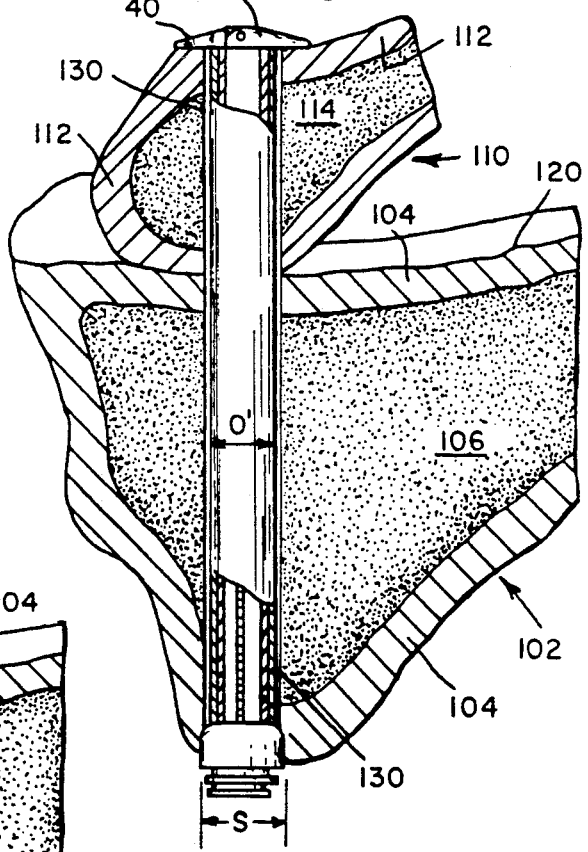

FIG. 8 is a cross-sectional view of two bones which have been placed relative to each other as shown in FIG. 7, and which have been denuded of cartilage at their adjacent surfaces in preparation for fusion, with the two bones being fastened together by the present invention winged compression bolt extending through the entire thickness of both bones with the spread wings resting on the outer surface of the cortex of one bone.

Figure 9:
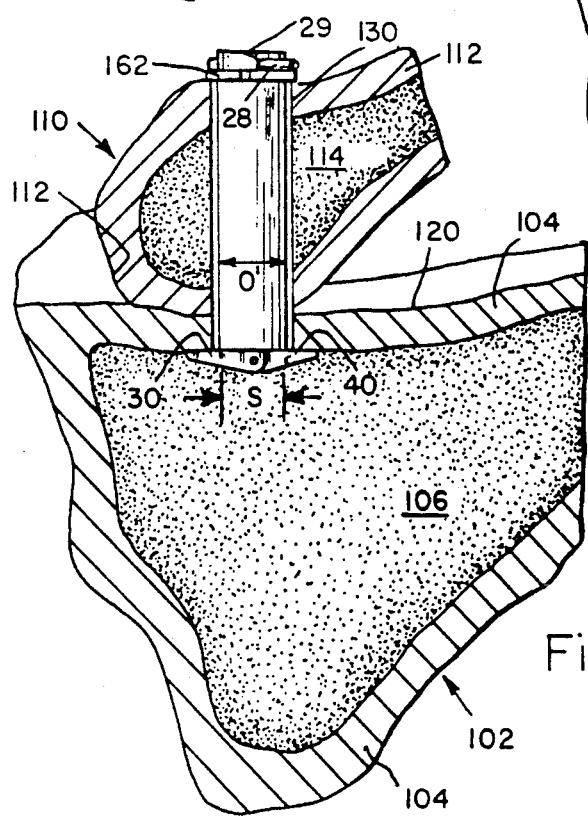

FIG. 9 is a cross-sectional view of two bones which have been placed relative to each other as shown in FIG. 7, and which have been denuded of cartilage at their adjacent surfaces, with the two bones being fastened together by the present invention winged compression bolt extending through the entire thickness of one bone and into the second bone such that the spread wings rests on the inner surface of the cortex of one bone and lie within the bone. Also shown is an alternative fastening means using a washer and cotter pin.

Figure 10:
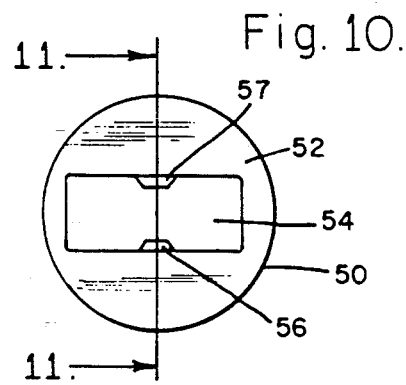

FIG. 10 is a bottom plan view of the preferred embodiment of the fastening means which is a collar having a tongue for mating engagement with ridges on the shaft.

FIG. 11 is a cross-sectional view of the preferred embodiment of the fastening means, taken along line 11—11 of FIG. 10.

Figure 12:
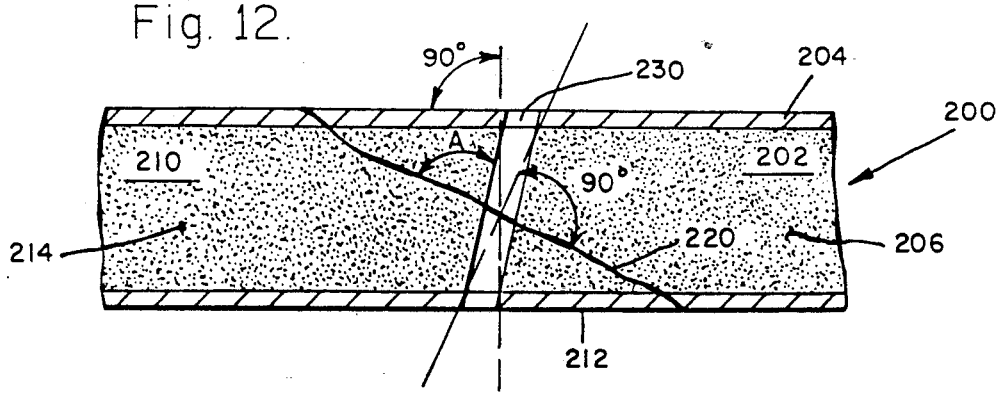

FIG. 12 is a cross-sectional view of a section of bone which has been fractured, illustrating the method by which the orientation of the drilled bore relative to the fracture line is computed, and also illustrating a bore being drilled through the bone to accommodate the present invention winged compression bolt.

FIG. 13 is a cross-sectional view of the section of fractured bone shown in FIG. 12, with the fractured sections being fastened together by the alternative embodiment use of the present invention winged compression bolt.

FIG. 14 is an end view of the section of fractured bone shown in FIG. 13, with the fractured sections being fastened together by the alternative embodiment use of the present invention winged compression bolt.

FIG. 15 is a top plan view of the section of fractured bone shown in FIG. 13, with the fractured sections being fastened together by the alternative embodiment use of the present invention winged compression bolt.

FIG. 16 is a perspective exploded view of the alternative embodiment fastening means internally threaded collar and threaded bolt.

FIG. 17 is a cross-sectional view of the alternative embodiment fastening means internally threaded collar and threaded bolt.

Figure 18:
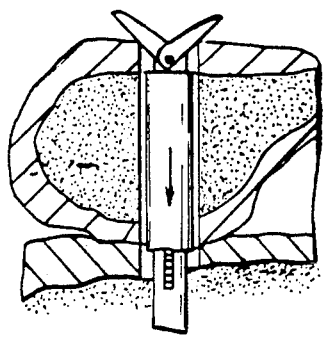

FIG. 18 is a cross-section of healed bone in which the wing compression bolt is being removed with the wings rotating and collapsing radially upward as the bolt is pulled out of the bone.

Figure 19:
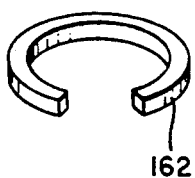

FIG. 19 is a spacing washer used to space cotter pin away from bone to create compression.

DETAILED DESCRIPTION OF THE PREFERRED EMBODIMENT

Although specific embodiments of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit, scope and contemplation of the invention as further defined in the appended claims.

Living bones are formed of cancellous material within a surrounding cortex. The compressive strength of compact cortical bone is 10,000 to 35,000 pounds per square inch whereas the cortex has a maximum shear strength of perhaps 15000 pounds per square inch. The cortex encases the much softer spongy cancellous bone which yields under very small pressures, particularly in shear. The present invention utilizes this fact to create a simple apparatus with few moving parts and which can be easily installed through bone portions and subsequently removed.

The present invention can be used to fuse adjacent bones together and can also be used to fixate two sections of broken bone together. The invention is the same for either application and therefore the details of the invention will be described first and then the applications will be illustrated.

Figure 1:
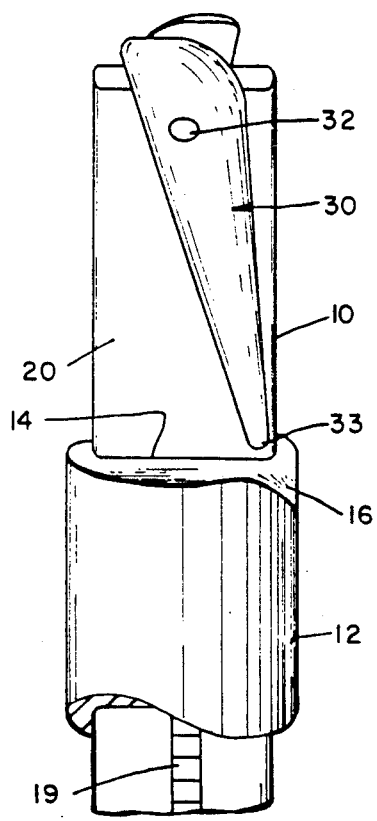
FIG. 1 is a side elevational view of the present invention winged compression bolt shown in the preferred configuration immediately before implantation through the bones or sections of a single bones.
Figure 2:
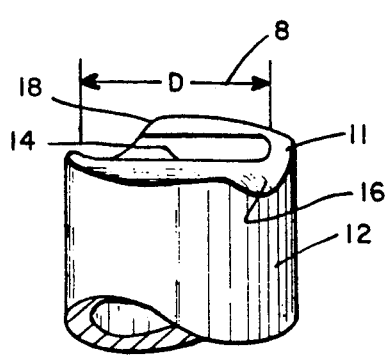
FIG. 2 is an enlarged perspective view of a portion of the upper end of the external hollow sleeve deployment device of the winged compression bolt.

A partial side elevational view of the present invention winged compression bolt 10 in the closed position is shown in FIG. 1. As will be discussed later on, the apparatus is shown in the preferred embodiment immediately prior to implantation through the bones. The main portions of the winged compression bolt 10 are an external hollow sleeve 12 (only a portion of which is shown), and internal shaft 20 supporting at least one wing 30, and a fastening or securing means 50 (illustrated in FIGS. 10 and 11). The front end or upper portion of external sleeve 12 is shown in greater detail in FIG. 2. In the preferred embodiment, the sleeve 12 is cylindrical with a retangular inner surface 6, but other cross-sections such as oval are within the spirit and scope of the present invention. The front or upper end 14 of sleeve 12 comprises at least one beveled section 16. In the preferred embodiment, there are a pair of oppositely disposed beveled sections 16 and 18. The thickness of the wall 11 of hollow sleeve 12 may range from 0.1 millimeters in its thinnest embodiment to 20 millimeters in its widest embodiment. The length of hollow sleeve 12 can range from 10 millimeters for its shortest embodiment to 80 millimeters for its longest embodiment. The wall 11 surrounds a centrally disposed rectangular opening 8 in external hollow sleeve 12. The inner diameter D of sleeve 12 can range from approximately 1.0 millimeters at its narrowest embodiment to approximately 6 millimeters at its widest embodiment.

Figure 3:
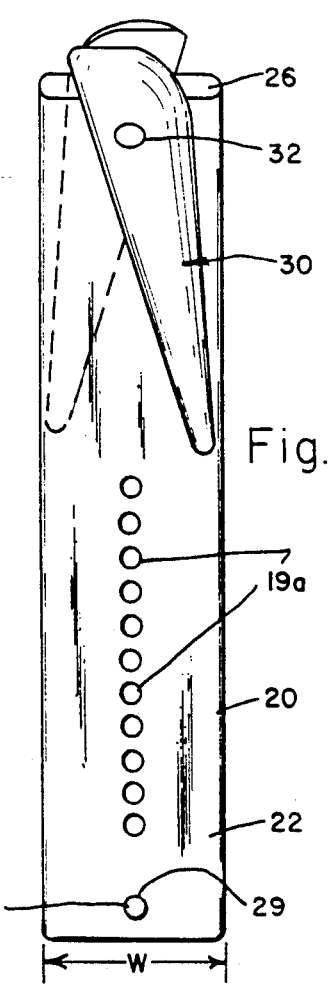
FIG. 3 is a side elevational view of the internal shank with wings in the folded position of the winged compression bolt with holes in shaft to provide an alternative fastening means.

A side elevational view of internal shaft 20 is shown in FIG. 3. In the preferred embodiment, internal shaft 20 is elongated and has a pair of oppositely disposed generally flat faces 22 and 24. The width W of internal shaft 20 is slightly less than the internal diameter D of opening 8 in elongated hollow sleeve 12 such that the shaft 20 can be movably and slidably inserted into elongated hollow sleeve 12 in a manner wherein the fit is almost a press fit such that the shaft 12 is at least partially retained by the wall 11 of elongated hollow sleeve 12. Shaft 20 further contains a multiply of aligned transverse ridges 19 (as illustrated un FIG. 1) which extend widthwise along the length of shaft 20. Supported adjacent the front or upper end 26 of shaft 20 is at least one wing or strut 30. A front elevational view of wing 30 by itself is shown in FIG. 4. Wing 30 is rotatably supported on shaft 20 by rotatable supporting means 32 (See FIG. 3) which by way of example can be a roll pin. Referring to FIG. 4, wing 30 comprises a central opening 34 whose diameter is wide enough to enable support means or roll pin 32 to fasten the wing 30 onto the shaft 20 in a manner which permits rotation of the wing 30 about the rotatable supporting means 32. Wing 30 has a lower straight edge surface 36 which when the wing is rotated to its open or fully extended position faces toward the lower end 28 of shaft 20. The remainder of the shape of the wing 30 is optional. In one embodiment, as illustrated in FIG. 4, the upper edge surface 38 of wing 30 is mostly straight and extends from one end of the lower straight edge surface 36 to a point above the straight edge and thereafter becomes curved and extends downwardly along curved edge surface 39 which joins the opposite end of lower straight edge surface 36. The thickness T of wing 30 can range from approximately 0.5 millimeters to approximately 10.0 millimeters and must provide the wing with a lower straight edge surface 36 of sufficient thickness to withstand a compressive force placed on it.

In the preferred embodiment, the shaft supports a pair of oppositely disposed wings 30 and 40. Wing 40 is shown in greater detail in FIG. 5. Wing 40 is identical to wing 30 and comprises a central opening 44 whose diameter is wide enough to enable rotatable support means or roll pin 32 to fasten the wing 40 onto the shaft 20 in a manner which permits rotation of the wing 40 about the rotatable supporting means 32. Wing 40 has a lower straight edge surface 46 which when the wing is rotated to its open or fully extended position faces toward the lower end 28 of shaft 20. The remainder of the shape of the wing 40 is optional. In one embodiment, as illustrated, the upper edge surface 48 of wing 40 is mostly straight and extends from one end of the lower straight edge surface 46 to a point above the straight edge and thereafter becomes curved and extends downwardly along curved edge surface 49 which joins the opposite end of lower straight edge surface 46. The thickness T of wing 40 can range from approximately 0.5 millimeters to approximately 10.0 millimeters and must provide the wing with a lower straight edge surface 46 of sufficient thickness to withstand a compressive force placed on it.

As shown in FIGS. 1, 3, and 6, wings 30 and 40 are mounted in an oppositely disposed orientation such that they open in an oppositely disposed direction. FIG. 6 is a front elevational view of the upper portion of shaft 20 with wings 30 and 40 in the fully opened position. Wing 30 on surface 22 is shown in solid lines and wing 40 on surface 24 is shown in partially solid and partially broken lines. In its fully extended position, wing 30 rotates about rotatable support means 32 until lower straight edge surface 36 is generally horizontal and faces toward lower end 28 of shaft 20. One end 31 of lower straight edge 36 extends past first edge 23 of shaft 20 for a short distance, for example from about 0.05 millimeters to about 2 millimeters. The opposite end 33 of lower straight edge surface 36 extends past second edge 25 of shaft 20 for a substantially longer distance, for example from about 2.0 millimeters to about 30 millimeters. In its fully extended position, wing 40 rotates about rotatable support means 32 until lower straight edge surface 46 is generally horizontal and faces toward lower end 28 of shaft 20. One end 41 of lower straight edge 46 extends past second edge 25 of shaft 20 for a short distance, for example from about 0.05 millimeters to about 2 millimeters. The opposite end 43 of lower straight edge surface 46 extends past first edge 23 of shaft 20 for a substantially longer distance, for example from about 2.0 millimeters to about 30 millimeters.

The methods by which the winged compression bolt 10 is used during an orthopedic surgery operation in fusing two adjacent bones is illustrated in FIGS. 8 and 9. The bones are illustrated in their relative orientation to each other in the perspective view of FIG. 7. In the first method, in FIG. 8 the winged compression bolt 10 extends entirely through both bones to be fused together. Two bones 102 and 110 are denuded of cartilage along interface line 120. The two bones 102 and 110 are pressed together along interface line 120. The first step is to drill an opening or bore 130 which extends from the cortex 104 of first bone 102, through the first section cancellous portion 106, across the opposite side of cortex 104, across the interface line 120, through the cortex 112 of second bone 110, and through the second section cancellous portion 114 of second bone section 110. The bore 130 is preferably cylindrical in order to provide a smooth surface through the sections of bone 102 and 110. The bore 130 is preferably perpendicular to the cortexes and the interface line but may be at angle angle less than 90 degrees to the bone shaft. The interface line 120 has been shown at the horizontal and therefore the bore 130 has been shown perpendicular to the cortexes 104 and 112. It will be appreciated that if the interface line 120 were at a different angle to the horizontal, the bore 130 could also be at an angle relative to the cortexes 104 and 112.

The inner diameter S of drilled bore 130 is intended to be slightly larger than the outside diameter D' of the elongated hollow sleeve 12. The preferred configuration immediately prior to insertion in bore 130 is shown in FIG. 1. The shaft 20 is set in the sleeve 12 to a point where the wings 30 and 40 fully extend out of the upper end 14 of sleeve 12. In addition, the wings 30 and 40 have been spread such that tip 33 of wing 30 is aligned with or resting on beveled section 16 of sleeve 12 and tip 43 of wing 40 is aligned with beveled section 18 of sleeve 12. The elongated hollow sleeve 12 with the internal shaft 20 within it and the wings 30 and 40 in the folded position as illustrated in FIG. 1 is then placed through bore 130 beginning at cortex 104, until the front or upper end 14 of sleeve 12 just extends past the remote cortex 112 located furthest from interface line 120. Preferably, the length of elongated hollow sleeve 12 has been chosen so as to correspond to the depth of the bone from the outer surface of one near cortex 104 through both bone sections 102 and 110 and immediately to the edge of the remote end of cortex 112. Then internal shaft 20 with the wings 30 and 40 spread as shown in FIG. 1 which are now at a distance beyond the outside of cortex 112 is caused to move downward such that the wings 30 and 40 travel in a direction back toward and radially outward of the elongated hollow sleeve 12 and cortex 112. It will be appreciated that the position as illustrated in FIG. 1 is necessary in order to get the spread motion of the wings started. By having aligned the tips 33 and 43 with beveled edges 16 and 18 respectively, as the shaft 20 is moved toward the cortex 112 and sleeve 12, the force of the upper end 14 of sleeve 12 pushes against the partially spread wings 30 and 40, causing them to spread further. The front edge 33 of lower straight edge surface 36 of wing 30 is caused to move along beveled portion 16 on the top of elongated hollow sleeve 12 and the front edge 43 of lower straight edge surface 46 of wing 40 is simultaneously caused to move along beveled portion 18 on the top of elongated hollow sleeve 12, thereby causing wing 30 to rotate in a counterclockwise direction about rotatable supporting means 32 and wing 40 to rotate in a clockwise direction about the same rotatable supporting means 32 until wings 30 and 40 are in their fully extended positions as shown in FIGS. 6 and 8. At such time as wing 30 has been rotated to a generally horizontal position, the opposite end 31 of lower straight edge surface 36 as in FIG. 6 comes in contact with a portion of wall 11 of external hollow sleeve 12 and stops further rotation of wing 30. Similarly, at such time as wing 40 has been rotated to a generally horizontal position, the opposite end 41 of lower straight edge surface 46 comes in contact with a portion of wall 11 of external hollow sleeve 12 and stops further rotation of wing 40. Wings 30 and 40 are therefore generally horizontally disposed and wing 30 is aligned such that its lower straight edge surface 36 abuts wall 11 of external hollow sleeve 12 and the portion of lower straight edge surface 36 in the area of end 33 lies against the exterior surface of cortex 112. Similarly, wing 40 is aligned such that its lower straight edge surface 46 abuts wall 11 of external hollow sleeve 12 and the portion of lower straight edge 46 in the area of end 43 lies against the exterior surface of cortex 112.

Fastening means 50 then serves to create a compression force wherein wings 30 and 40 are compressed against the exterior of cortex 112. The preferred embodiment is a horizontal ratchet arrangement. A bottom plan view of the partially internally tongued collar 52 is illustrated in FIG. 10 and a cross-sectional view is illustrated in FIG. 11. The internally tongued collar 52 contains an internal opening 54 having tongues 56 and 57 on the lower portion of its wall 58 which protrude into the opening 54. The tongued collar 52 is pushed on shaft 20 at its lower end 28 such that the opening 54 fits around shaft 20 and the tongues 56 and 57 grab onto the ridges 19 on the faces of the shank. The hollow tongued collar 52 is pushed on shaft 20 until the top 59 of the wall of the collar 52 is tightened against the lower end 13 of external hollow sleeve 12 and also tightened against the exterior of cortex 104, to thereby create a press fit, and thereby causing the wings 30 and 40 to be tightened against the cortex 112 and upper end 14 of internal hollow sleeve 12. The initial tightening and relative tightening of ratchet collar 52 against the internal shaft ratchets 19 may be performed by hand or with an appropriate tool. For added tightness, a hole 29 may be drilled through the shank 20 immediately below the tightened collar 52 and a cotter pin or other fixation means 60 inserted through the hole to assure that the collar 52 will not slip and loosen the compression fit. In this manner, a compression bond is formed wherein the two bones 102 and 110 are tightened together along the interface line 120 and held in place through the compression which is the strongest force the bones can withstand (as opposed to tensile or shear). It will be appreciated that the press fit tongued collar 52 is only one fastening means 50 which can be used to achieve the desired result. Should play exist between the bone and the cotter pin 52, slotted washer (s) 162 of varied sizes can fit around the outer sleeve 12 and up to the cotter pin 60 to press against bone surface 104.

An alternative method for use of the winged compression bolt 10 in fusing two bones together is illustrated in FIG. 9. In this method, the wings 30 and 40 lie within the first bone 102. Two bones 102 and 110 are denuded of cartilage along interface line 120. The two bones 102 and 110 are fit together along interface line 120. The first step is to drill an opening or bore 130 which extends from the cortex 112 of second bone 110, through the second section cancellous portion 114, across the opposite side of cortex 112, across the interface line 120, through the cortex 104 of first bone 102, and through the first section cancellous portion 106 of first bone section 102. The bore 130 is preferably cylindrical in order to provide a smooth surface through the sections of bone 102 and 110. The bore 130 is preferably perpendicular to the cortexes and the interface line but may be at angle angle less than 90 degrees. The interface line 120 has been shown at the horizontal and therefore the bore 130 has been shown appreciated that if the interface line 120 were at a different angle to the horizontal, the bore 130 would also be at an angle relative to the cortexes 104 and 112.

The inner diameter S of drilled bore 130 is intended to be slightly larger than the outside diameter D' of the elongated hollow sleeve 12. The preferred configuration immediately prior to insertion in bore 130 is shown in FIG. 1. The shaft 20 is set in the sleeve 12 to a point where the wings 30 and 40 fully extend out of the upper end 14 of sleeve 12. In addition, the wings 30 and 40 have been spread such that tip 33 of wing 30 is aligned with beveled section 16 of sleeve 12 and tip 43 of wing 40 is aligned with beveled section 18 of sleeve 12. The elongated hollow sleeve 12 with the internal shank 20 within it and the wings 30 and 40 in the folded position as illustrated in FIG. 3 is then placed through bore 130 beginning at cortex 112, until the front or upper end 14 of sleeve 12 just extends past the cortex 104 located adjacent interface line 120. Preferably, the length of elongated hollow sleeve 12 has been chosen so as to correspond to the depth of the bone from the outer surface of one near cortex 112 to the interior of the cortex 104 of first bone 102 which lies adjacent to interface line 120. Then internal shaft 20 with the wings 30 and 40 spread as shown in FIG. 1 which are now at a distance beyond the cortex 104 is caused to move downward such that the wings 30 and 40 travel in a direction back toward and radially outward of the elongated hollow sleeve 12 and cortex 104. It will be appreciated that the position as illustrated in FIG. 1 is necessary in order to get the spread motion of the wings started. By having aligned the tips 33 and 43 with beveled edges 16 and 18 respectively, as the shaft 20 is moved toward the cortex 104 and sleeve 12, the force of the upper end 14 of sleeve 12 pushes against the partially spread wings 30 and 40, causing them to spread further. The front edge 33 of lower straight edge surface 36 of wing 30 is caused to move along beveled portion 16 on the top of elongated hollow sleeve 12 and the front edge 43 of lower straight edge surface 46 of wing 40 is simultaneously caused to move along beveled portion 18 on the top of elongated hollow sleeve 12, thereby causing wing 30 to rotate in a counterclockwise direction about rotatable supporting means 32 and wing 40 to rotate in a clockwise direction about rotatable supporting means 42 until wings 30 and 40 are in their fully extended positions as shown in FIGS. 6 and 9. At such time as wing 30 has been rotated to a generally horizontal position, the opposite end 31 of lower straight edge surface 36 comes in contact with a portion of wall 11 of external hollow sleeve 12 and stops further rotation of wing 30. Similarly, at such time as wing 40 has been rotated to a generally horizontal position, the opposite end 41 of lower straight edge surface 46 comes in contact with a portion of wall 11 of external hollow sleeve 12 and stops further rotation of wing 40. Wings 30 and 40 are therefore generally horizontally disposed and wing 30 is aligned such that its lower straight edge surface 36 abuts wall 11 of external hollow sleeve 12 and the portion of lower straight edge surface 36 in the area of end 33 lies against the interior surface of cortex 112. Similarly, wing 40 is aligned such that its lower straight edge surface 46 abuts wall 11 of external hollow sleeve 12 and the portion of lower straight edge 46 in the area of end 43 lies against the interior surface of cortex 104.

Fastening means of a cotter pin through the holes in the inner shaft is used to secure the outer sleeve to maintain its pressure against the wings. In FIG. 19 a slotted washer is used to take up slack between the bone surface and the cotter pin. This washer is in place in FIG. 9 at the space between bone and cotter pin. The washer may be of varied thicknesses to take up the slack. It is within the spirit and scope of the present invention to have only one wing 30 or 40 however the pair of wings 30 and 40 provide a more balanced compressive force and is the preferred embodiment. It is also within the spirit and scope of the present invention for the shaft 20 be cylindrical or oval and conform more closely to the shape of sleeve 12.

After the bones 102 and 110 have healed, the winged compression bolt 10 can be removed by removing the fastening means such as the tongued collars 52, and pulling the shaft 20 in a downward direction as shown in FIG. 18 where the tips 31 and 41 push the outer sleeve downward on the inner shank. In the embodiment in FIGS. 8, 9, 12 and 18, the tips of the wings 30 and 40 are caused to rotate away from cortex 112 until edges 33 and 43 respectively are almost centrally disposed on shaft 20 and the lower straight edges 36 and 46 respectively are almost vertical. The force on the shaft is then continued and the shaft 20 with folded wings 30 and 40 and the external hollow sleeve 12 are then pulled out of the bone as they are moved away from cortex 112 toward cortex 104. The opening left in shaft 130 will heal in time. Alternatively, once the tongued collar 52 is removed, the sleeve 12 can be pulled out first, the shank 20 can be pulled outward and the wings 30 and 40 will fold upwardly such that tips 33 and 43 point away from the top 26 of shaft 20 and then shank and wings are pulled out.

The external hollow sleeve 12 can be made of any suitable material having appropriate compression strength, such as nylon, steel, titanium, etc. The collar 52 can be made with tongue of any resilient inert material. The internal ratcheted shaft 20 is preferably made of resilient inert material but can be made of other suitable material such as metal.

The alternative use of the present invention is illustrated in FIGS. 12 through 15. Referring to FIG. 12, there is illustrated at 200 a section of bone such as a human leg bone. The bone 200 has been broken in one place which is illustrated as fracture line 220 and therefore has been broken into two sections 202 and 210. First bone section 202 has the exterior cortex 204 and the interior cancellous portion 206. Second bone section 210 has the exterior cortex 212 and the interior cancellous portion 214. The first step following reduction of the fractured pieces so they are in close proximity and virtually aligned is to drill an opening or bore 230 which extends from the cortex 204 of first bone section 202, through the first section cancellous portion 206, across the fracture line 220, through the second section cancellous portion 214 and through the cortex 212 of second bone section 210. The bore 230 is preferably cylindrical and slightly larger than the outer sleeve of the present invention in order to provide a smooth surface through the sections of bone 200. The bore 230 is at an angle A to the bone surface 207. Angle "A" is determined as follows. Referring to FIG. 12, first, a line L1 is drawn which is perpendicular to the two cortexes 204 and 212. Then a second line L2 is drawn which is perpendicular to the fracture line 220. The angle between the lines L1 and L2 is measured and is divided in half. The bore 230 is drilled along this bisecting line between lines L1 and L2. It is found that this orientation provides the strongest compressive force with the most stability to heal the broken sections of bone.

The method by which the present invention winged compression bolt 10 is used for fixation of two sections of broken bone during an orthopedic surgery operation is shown in the cross-sectional view of FIG. 13. A bone 200 is fractured along line 220 and the bone is broken into sections 202 and 210. The two sections 202 and 210 of bone 200 are examined and manipulated so they fit together along fracture line 220. The first step is to drill an opening or bore 230 which extends from the cortex 204 of first bone section 202, through the first section cancellous portion 206, across the fracture line 220, through the second section cancellous portion 214 and through the cortex 212 of second bone section 210. The bore 230 is at the angle "A" relative to the fracture line. The bore 230 is preferably cylindrical and slightly larger than the outer sleeve 12 in order to provide a smooth surface through the sections of bone 200 for the device to be inserted. In most cases, the preferred angle "A" is between 113 and 90 degrees. In FIG. 13, the fracture line 220 has been shown at a 45 degree angle to the horizontal and therefore the shaft 230 has been shown perpendicular to the cortexes 204 and 212 for illustration purposes only.

The diameter S of bore 230 is intended to be slightly larger than the outside diameter D' of the elongated hollow sleeve 12. The preferred configuration immediately prior to insertion in bore 230 is shown in FIG. 1. The shaft 20 has been inserted into sleeve 12 to a point where the wings 30 and 40 fully extend out of the upper end 14 of sleeve 12 such that the tips just touch sleeve 12. In addition, the wings 30 and 40 have been spread such that tip 33 of wing 30 is aligned with beveled section 16 of sleeve 12 and tip 43 of wing 40 is aligned with beveled section 18 of sleeve 12. The elongated hollow sleeve 12 with the internal shaft 20 within it and the wings 30 and 40 in the folded position as illustrated in FIG. 1 is then placed through bore 230 beginning at cortex 212, until the front or upper end 14 of sleeve 12 just abuts the outer surface of cortex 204. Preferably, the length of elongated hollow sleeve 12 has been chosen so as to correspond to the depth of the bone from the outer surface of one cortex to the outer surface of the opposite cortex. However, if this has not been done, the elongated hollow sleeve 12 which remains in bore 230 is cut at its rear or lower end 13 until its length is approximately equal to the depth of the bone 200 from cortex to cortex. Then internal shaft 20 with the wings 30 and 40 spread as shown in FIG. 1 which are now at a distance beyond cortex 204 is caused to move downward such that the wings 30 and 40 travel in a direction back toward and radially outward of the elongated hollow sleeve 12 and cortex 204. It will be appreciated that the position as illustrated in FIG. 1 is necessary in order to get the spread motion of the wings started. By having aligned the tips 33 and 43 with beveled the bone 200 and sleeve 12, the force of the upper end 14 of sleeve 12 pushed against the partially spread wings 30 and 40, causes them to spread further. The front edge 33 of lower straight edge surface 36 of wing 30 is caused to move along and the front edge 43 of lower straight edge surface 46 of wing 40 is simultaneously caused to move along beveled portion 18 on the top of elongated hollow sleeve 12, thereby causing wing 30 to rotate in a counterclockwise direction about rotatable supporting means 32 and wing 40 to rotate in a counterclockwise direction about rotatable supporting means 32 until wings 30 and 40 are in their fully extended positions as shown in FIGS. 6 and 13. At such time as wing 30 has been rotated to a generally horizontal position, the opposite end 31 of lower straight edge surface 36 comes in contact with a portion of wall 11 of external hollow sleeve 12 and stops further rotation of wing 30. Similarly, at such time as wing 40 has been rotated to a generally horizontal position, the opposite end 41 of lower straight edge surface 46 comes in contact with a portion of wall 11 of external hollow sleeve 12 and stops further rotation of wing 40. Wings 30 and 40 are therefore generally horizontally disposed and wing 30 is aligned such that its lower straight edge surface 36 abuts wall 11 of external hollow sleeve 12 and the portion of lower straight edge surface 36 in the are of end 33 lies against the outer surface of cortex 204. Similarly, wing 40 is aligned such that its lower straight edge surface 46 abuts wall 11 of external hollow sleeve 12 and the portion of lower straight edge 46 in the area of end 43 lies against the outer surface of cortex 204. The spread of the wings 30 and 40 on the outer surface of cortex 204 is also illustrated in the top plan view of FIG. 15.

Fastening means 50 then serves to create a compression force wherein wings 30 and 40 are compressed against cortex 204. It will be be appreciated that the tongued collar 52 can be utilized with this method and the process of affixing and locking in the tongued collar and the additional support of the bored hole and cotter pin can also be used. However, an alternative fastening means 50 will be described and is illustrated in FIGS. 13 and 14 and in individual detail in FIGS. 16 and 17. It will be appreciated that this alternative fastening means can also be used with the method of fusing two bones together as previously described. Referring to FIG. 13, and also to FIGS. 16 and 17, in one type of fastening means 250, the lower end 28 is press fitted with a partially internally threaded collar 252 which contains an internal opening 254 having threads 256 on the lower portion of its wall 258. A mating male bolt 260 having threads 262 on its wall 264 is then screwed into the collar 252 until the bolt 260 is tightened against the lower end 259 of collar 252 and just above an opening 29 in shaft 20. A cotter pin 60 or other suitable locking means is then inserted through the opening 29 to cause bolt 260 to remain fixed relative to shaft 20. The threaded collar 252 is then rotated about fixed bolt 260 such that the threaded collar moves upwards on bolt 260 and then collar 252 is tightened against the bone thereby causing the wings 30 and 40 to be tightened against the cortex 204 and upper end 14 of internal hollow sleeve 12. The initial bolt tightening and relative rotation of collar 252 to the fixed bolt 260 may be performed by hand or with an appropriate tool such as a wrench. In this manner, a compression bond is formed wherein the two sections of bone 202 and 210 are tightened together along the fracture line 230 and held in place through the compression which is the strongest force the bone 200 can withstand (as opposed to tensile or shear). It will be appreciated that the press fit collar 252 and threaded bolt 260 are only one fastening means 250 which can be used to achieve the desired result.

Alternatively, the cotter pin as in FIG. 9 can be pushed through the lowermost opening 29 which abuts lower end 13 of external hollow sleeve 12 and the outer surface of cortex 206 to create a compression fit with possible use of shims 162 to take up slack. Where appropriate, this cotter pin 60 arrangement can be used instead of the press fit collar 252 and bolt 260 but preferably is used in conjunction with the press fit collar and bolt as previously described.

For this alternative embodiment, it is also within the spirit and scope of the present invention to have only one wing 30 or 40 however the pair of wings 30 and 40 provide a more balance compressive force and is the preferred embodiment.

It is also within the spirit and scope of the present invention for the shaft 20 to be cylindrical or oval and conform more closely to the shape of the sleeve 12.

As illustrated in FIG. 18, after the bone 200 has healed, the winged compression bolt 10 can be removed by removing cotter pin 60, removing the bolt 260 and the press fit collar 252, and pulling downward pulling the shaft 20 in a downward direction so that the wings 30 and 40 are caused to move away from cortex 204 until the tips of the wings 33 and 43 respectively are no longer in contact with the bone. The direction of force on the shaft is then continued, the wings rotate up opposite to pull and the shaft 20 with folded wings 30 and 40 above the external hollow sleeve 12 are then pulled out of the bone as they are moved away from cortex 204 toward cortex 212. The opening left in shaft 230 will heal in time. Alternatively, after the press fit collar 252 is removed, the sleeve 12 is pulled out first. The shaft is then pulled out. With no sleeve 12 to support the wings 30 and 40 there is less resistance and the wings fold inwardly with their tips 33 and 43 pointing away from the top 26 of shaft 20 and are aligned on the shaft 20, thereby providing no resistance.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the invention might be embodied or operated.

The invention has been described in considerable detail in order to comply with the patent laws by providing full public disclosure of at least one of its forms. However, such detailed description is not intended in any way to limit the broad features or principles of the invention, or the scope of patent monopoly to be granted.

What is claimed is:

1. A winged compression bolt for fusing a first bone having a cortex and an interior portion to a second bone having a cortex and interior portion together at a location where the cortexes of the two bones are set adjacent one another, comprising:
   a. a hollow outer sleeve having a sidewall enclosing a centrally disposed opening within the sleeve, a front end and a rear end;
   b. the length of said hollow outer sleeve being approximately equal to the longest distance from the cortex of the first bone to the cortex of the second bone at the location where the two bones are laid adjacent each other to be fused together;
   c. an elongated shaft having a front end and a rear end and which is movably set in the opening in said hollow outer sleeve;
   d. the length of said elongated shaft being greater than the length of said hollow outer sleeve such that both the front end and the rear end of the elongated shaft extend beyond the hollow outer sleeve;
   e. at least one rotatable wing having a straight edge and rotatably supported on said shaft adjacent the front end of said shaft; and
   f. a securing means located adjacent the rear end of said shaft;
   g. whereby when the two bones are aligned adjacent one another for a portion of their length, a bore extending from the cortex of the first bone through its interim portion, through the adjacent cortex portions of the first and second bones, through the interior portion of the second bone and through the outer cortex of the second bone can accommodate the winged compression bolt by having said hollow outer sleeve and inner elongated shaft inserted through the bore such that the front end of the hollow outer sleeve lies adjacent the outer surface of the cortex of the second bone and the rear end of the hollow outer sleeve lies adjacent the remote outer surface of the cortex of the first bone such that the straight edge of said at least one rotatable wing lies along the outer surface of the cortex of said second bone and also touches the surface of the front end of the hollow outer sleeve and said securing means is tightened against the remote surface of the cortex of the first bone to thereby provide a compressive force generated between said at least one rotatable wing and the securing means to thereby provide a compressive force to fuse the two bones together.

2. A winged compression bolt for fusing a first bone having a cortex and an interior portion to a second bone having a cortex and interior cancellous portion together at a location where the cortexes of the two bones are set adjacent one another, comprising:
   a. a hollow outer sleeve having a sidewall enclosing a centrally disposed opening within the sleeve, a front end and a rear end;
   b. the length of said hollow outer sleeve being approximately equal to the distance from the cortex of the first bone at its location remote from the location where the cortexes of the first and second bones are adjacent each other to the interior of the cortex of the second bone at the location where the cortexes of the first and second bones are adjacent each other, when the two bones are laid adjacent each other to be fused together;
   c. an elongated shaft having a front end and a rear end and which is movably set in said hollow outer sleeve;
   d. the length of said elongated shaft being greater than the length of said hollow outer sleeve such that both the front end and the rear end of the elongated shaft extend beyond the hollow outer sleeve;
   e. at least one rotatable wing having a straight edge and rotatably supported on said shaft adjacent the front end of said shaft; and
   f. a securing means located adjacent the rear end of said shaft;
   g. whereby when the two bones are aligned adjacent one another for a portion of their length, a bore extending entirely through the first bone and extending into the second bone past the interior of the cortex and into its cancellous portion can accommodate the winged compression bolt by having said hollow outer sleeve and inner elongated shaft inserted through the bore such that the front end of the hollow outer sleeve lies within the second bone and adjacent the interior of the cortex of the second bone at the location where the cortexes of the first and second bones are adjacent each other, and the rear end of the hollow outer sleeve lies adjacent the remote outer surface of the cortex of the first bone such that the straight edge of said at least one rotatable wing lies along the interior surface of the cortex of said second bone at the location where the cortexes of the first and second bones are adjacent each other, and also touches the surface of the front end of the hollow outer sleeve, and said securing means is tightened against the remote surface of the cortex of the first bone to thereby provide a compressive force generated between said at least one rotatable wing and the securing means to thereby provide a compressive force to fuse the two bones together.

3. A winged compression bolt in accordance with claims 1 or 2 wherein said securing means further comprises a hollow collar having threads along a portion of its interior wall and fit around the rear end of said hollow outer sleeve, and a threaded bolt threaded into said hollow collar and press fit against said hollow sleeve such that said hollow collar can be rotated relative to the threaded bolt and tightened against the remote surface of the cortex of the first bone.

4. A winged compression bolt in accordance with claims 1 or 2 wherein said elongated shaft further comprises a multiplicity of ridges on at least one of its lateral surfaces and said securing means further comprises a hollow collar having at least one tongue protruding inwardly whereby the hollow collar can be affixed to the elongated shaft by a mating of the at least one tongue with at least one ridge on the elongated shaft and the hollow collar is further press fit against the remote outer surface of the hollow sleeve.

5. A winged compression bolt in accordance with claims 1 or 2 wherein said elongated shaft further comprises a multiplicity of holes through its width and said securing means comprises a pin which can be placed through one of said holes in the elongated shaft and the pin is press fit against the outer hollow sleeve.

6. A winged compression bolt in accordance with claims 1 or 2 wherein a washer may be placed between said securing means and bone surface to create compression on the cortexes of bone.

7. A winged compression bolt for fusing a first bone having a cortex and an interior portion to a second bone having an outer cortex and interior cancellous portion together at a location where the cortexes of the two bones are set adjacent one another, comprising:
 a. a hollow outer sleeve further comprising a sidewall enclosing a centrally disposed opening extending through the sleeve, a front end including a pair of oppositely disposed beveled sections in the sidewall, and a rear end;
 b. the length of said hollow outer sleeve being approximately equal to the longest distance from the cortex of the first bone to the cortex of the second bone at the location where the two bones are laid adjacent each other to be fused together;
 c. an elongated shaft having a front end and a rear end and which is movably set in said hollow sleeve;
 d. the length of said elongated shaft being greater than the length of said hollow outer sleeve such that both the front end and the rear end of the elongated shaft extend beyond the hollow outer sleeve;
 e. a first rotatable wing having a straight edge;
 f. a second rotatable wing having a straight edge;
 g. said first rotatable wing rotatably supported on one side of said shaft and adjacent the front end of said shaft;
 h. said second rotatable wing rotatably supported on the side of said shaft opposite to the side supporting said first wing, and adjacent the front end of said shaft such that the second wing is oppositely disposed to the first wing; and
 i. a securing means located adjacent the rear end of said shaft;
 j. whereby when the two bones are aligned adjacent one another for a portion of their length, a bore extending from the cortex of the first bone through its interior portion, through the adjacent cortex portions of the first and second bones, through the portion of the second bone and through the interior cortex of the second bone can accommodate the winged compression bolt by having said hollow outer sleeve and inner elongated shaft inserted through the bore such that the front end of the hollow outer sleeve lies adjacent the outer surface of the cortex of the second bone and the rear end of the hollow outer sleeve lies adjacent the remote outer surface of the cortex of the first bone such that the straight edge of said first wing can be rotated relative to said elongated shaft such that its straight edge can move along one beveled edge on the front edge of the hollow sleeve and become aligned generally parallel to and lie along the outer surface of the cortex of said second bone and also touches the surface of the front end of the hollow outer sleeve and said second wing can be rotated relative to said shaft such that its straight edge can move along the opposite beveled edge on the front edge of the hollow sleeve and become aligned generally parallel to and lie along the outer surface of the cortex of said second bone and also touches the surface of the front end of the hollow outer sleeve and extend in the direction opposite to the direction of the straight edge of the first wing, and said securing means is tightened against the remote surface of the cortex of the first bone to thereby provide a compressive force generated between said first and second rotatable wings and the securing means to thereby provide a compressive force to fuse the two bones together.

8. A winged compression bolt for fusing a first bone having an outer cortex and an interior portion to a second bone having an outer cortex and interior portion together at a location where the cortexes of the two bones are set adjacent one another, comprising:
 a. a hollow outer sleeve further comprising a sidewall enclosing a centrally disposed opening extending through the sleeve, a front end including a pair of oppositely disposed beveled sections in the sidewall, and a rear end;
 b. the length of said hollow outer sleeve being approximately equal to the distance from the cortex of the first bone at its location remote from the location where the cortexes of the first and second bones are adjacent each other to the interior of the cortex of the second bone at the location where the cortexes of the first and second bones are adjacent each other, when the two bones are laid adjacent each other to be fused together;
 c. an elongated shaft having a front end and a rear end and which is movably set in said hollow sleeve;
 d. the length of said elongated shaft being greater than the length of said hollow outer sleeve such that both the front end and the rear end of the elongated shaft extend beyond the hollow outer sleeve;
 e. a first rotatable wing having a straight edge;
 f. a second rotatable wing having a straight edge;

g. said first rotatable wing rotatably supported on one side of said shaft and adjacent the front end of said shaft;
h. said second rotatable wing rotatably supported on the side of said shaft opposite to the side supporting said first wing, and adjacent the front end of said shaft such that the second wing is oppositely disposed to the first wing; and
i. a securing means located adjacent the rear end of said shaft;
j. whereby when the two bones are aligned adjacent one another for a portion of their length, a bore extending entirely through the first bone and extending into the second bone past the cortex and into its interior portion can accommodate the winged compression bolt by having said hollow outer sleeve and inner elongated shaft inserted through the bore such that the front end of the hollow outer sleeve lies within the interior of the second bone at the location where the cortexes of the first and second bones are adjacent each other, and the rear end of the hollow outer sleeve lies adjacent the remote surface of the cortex of the first bone such that the straight edge of said first wing can be rotated relative to said elongated shaft such that its straight edge can move along one beveled edge on the front edge of the hollow sleeve and become aligned generally parallel to and lie along the interior surface of the outer cortex of said second bone at the location where the cortex of the first and second bones are adjacent each other, and also touches the surface of the front end of the hollow outer sleeve, and said second wing can be rotated relative to said shaft such that its straight edge can move along the opposite beveled edge on the front edge of the hollow sleeve and become aligned generally parallel to and lie along the interior surface of said second bone at the location where the cortex of the first and second bones are adjacent each other, and also touches the surface of the front end of the hollow outer sleeve and extend in the direction opposite to the direction of the straight edge of the first wing, and said securing means is tightened against the remote surface of the cortex of the first bone to thereby provide a compressive force generated between said first and second rotatable wings and the securing means to thereby provide a compressive force to fuse the two bones together.

9. A winged compression bolt in accordance with claims 7 or 8 wherein said securing means further comprises a hollow collar having threads along a portion of its interior wall and fit around the rear end of said hollow outer sleeve, and a threaded bolt threaded into said hollow collar and press fit against said hollow sleeve such that said hollow collar can be rotated relative to the fixed bolt and tightened against the remote outer surface of the cortex of the first bone.

10. A winged compression bolt in accordance with claims 7 or 8 wherein said elongated shaft further comprises a multiplicity of ridges on at least one of its lateral surfaces and said securing means further comprises a hollow collar having at least one tongue protruding inwardly whereby the hollow collar can be affixed to the elongated shaft by a mating of the at least one tongue with at least one ridge on the elongated shaft and the hollow collar is further press fit against the remote outer surface of the hollow sleeve.

11. A winged compression bolt in accordance with claims 7 or 8 wherein said elongated shaft further comprises a multiplicity of holes through its width and said securing means comprises a pin which can be placed through one of said holes in the elongated shaft and the pin is press fit against the outer hollow sleeve.

12. A winged compression bolt in accordance with claims 7 or 8 wherein a washer may be placed between said securing means and bone surface to create compression on the cortexes of bone.

13. A winged compression bolt for fusing first and second bones together comprising:
    a. a hollow outer sleeve having a sidewall enclosing a centrally disposed opening within the sleeve, a front end and a rear end:
    b. an elongate shaft having a front end and a rear end and which is movably set in the opening in said hollow outer sleeve;
    c. at least one wing having a straight edge and rotatably supported via pivot means on said shaft front end;
    d. wherein said shaft front end and said pivot means extend beyond the front end of said hollow outer sleeve and said wing is rotatable into a deployed position.

14. The invention in accordance with claim 13 wherein said
    hollow outer sleeve is moved against said wing causing it to rotate into the deployed position.

15. The invention in accordance with claim 13 further comprising means for
    providing a compressive force, said means comprising a pair of oppositely disposed wings each wing having a straight edge aligned against an edge of the hollow outer sleeve and against an adjacent exterior surface of the second bone when said wings are in the deployed position.

16. The invention in accordance with claim 13 further comprising
    a securing means on the rear end of the shaft which is tightened against the shaft and the exterior surface of the first bone remote from the second bone to create a compressive force between a said wing and the securing means.

17. A winged compression bolt for fusing sections of bone together comprising:
    a. a hollow outer sleeve having a sidewall enclosing a centrally disposed opening within the sleeve, a front end and a rear end:
    b. an elongate shaft having a front end and a rear end and which is movably set in the opening in said hollow outer sleeve;
    c. at least one wing having a straight edge and rotatably supported via pivot means on said shaft front end;
    d. wherein said shaft front end and said pivot means extend beyond the front end of said hollow outer sleeve and said wing is rotatable into a deployed position to provide a compressive force against a surface of the cortex of a bone.

18. The invention in accordance with claim 17 wherein said
    hollow outer sleeve is moved against said wing causing it to rotate into the deployed position.

19. The invention in accordance with claim 17 further comprising means for
    providing a compressive force, said means comprising a pair of oppositely disposed wings each wing having a straight edge aligned against an edge of the hollow outer sleeve and against an adjacent portion of the internal surface of the bone when said wings are in the deployed position.

20. The invention in accordance with claim 17 further comprising
   a securing means on the rear end of the shaft which is tightened against the shaft and the exterior surface of the bone remote from said wing to create a compressive force between said wing and the securing means.

21. A winged compression bolt for fixating broken sections of a bone, comprising:
   a. a hollow outer sleeve having a sidewall enclosing a centrally disposed opening within the sleeve, a front end and a rear end;
   b. the length of the hollow outer sleeve being approximately equal to the width of the combined sections of broken bone at the location where the sections are being fixated together;
   c. an elongated shaft having a front end and a rear end and which is movably set in said hollow outer sleeve;
   d. the length of said elongated shaft being greater than the length of said hollow outer sleeve such that both the front end and the rear end of the elongated shaft extend beyond the hollow outer sleeve;
   e. at least one rotatable wing having a straight edge and rotatably supported on said shaft adjacent the front end of said shaft; and
   f. a securing means located adjacent the rear end of said shaft;
   g. whereby a bore extending through the sections of broken bone and intersecting the area of fracture can accommodate the winged compression bolt by having said hollow outer sleeve and inner elongated shaft inserted through the bore such that the front end of the hollow outer sleeve lies adjacent one outer surface of the broken bone and the rear end of the hollow outer sleeve lies adjacent the opposite outer surface of the broken bone such that the straight edge of said at least one rotatable wing lies along the front edge of said hollow outer sleeve and an adjacent section of outer bone surface and said securing means is tightened against said rear end of said hollow outer sleeve to thereby provide a compressive force generated between said at least one rotatable wing and the securing means to thereby provide a compressive force to fixate the broken sections of bone together.

22. A winged compression bolt in accordance with claim 21 wherein said securing means further comprises a hollow collar having threads along a portion of its interior wall and fit around the rear end of said hollow outer sleeve, and a threaded bolt threaded into said hollow collar and press fit against said hollow sleeve such that said hollow collar can be rotated relative to the fixed bolt and tightened against the remote surface of the cortex of the bone.

23. A winged compression bolt in accordance with claim 21 wherein said elongated shaft further comprises a multiplicity of ridges on at least one of its lateral surfaces and said securing means further comprises a hollow collar having at least one tongue protruding inwardly whereby the hollow collar can be affixed to the elongated shaft by a mating of the at least one tongue with at least one ridge on the elongated shaft and the hollow collar is further press fit against the remote outer surface of the hollow sleeve.

24. A winged compression bolt in accordance with claim 21 wherein said elongated shaft further comprises a multiplicity of holes through its width and said securing means comprises a pin which can be placed through one of said holes in the elongated shaft and the pin is press fit against the outer hollow sleeve.

25. A winged compression bolt in accordance with claim 21 wherein a washer may be placed between said securing means and bone surface to create compression on the cortexes of bone.

26. A winged compression bolt for fixating broken sections of bone, comprising:
   a. a hollow outer sleeve further comprising a sidewall enclosing a centrally disposed opening extending through the sleeve, a front end including a pair of oppositely disposed beveled sections in the sidewall, and a rear end;
   b. the length of the hollow outer sleeve being approximately equal to the width of the combined sections of broken bone at the location where the sections are being fixated together;
   c. an elongated shaft having a front end and a rear end and which is movably set in said hollow outer sleeve;
   d. the length of said elongated shaft being greater than the length of said hollow outer sleeve such that both the front end and the rear end of the elongated shaft extend beyond the hollow outer sleeve;
   e. a first rotatable wing having a straight edge;
   f. a second rotatable wing having a straight edge;
   g. said first rotatable wing rotatably supported on one side of said shaft and adjacent the front end of said shaft;
   h. said second rotatable wing rotatably supported on the side of said shaft opposite to the side supporting said first wing, and adjacent the front end of said shaft such that the second wing is oppositely disposed to the first wing; and
   i. a securing means located adjacent the rear end of said shaft;
   j. whereby a bore extending through the sections of broken bone and intersecting the area of fracture can accommodate the winged compression bolt by having said hollow outer sleeve and inner elongated shaft inserted through the bore such that the front end of the hollow outer sleeve lies adjacent one outer surface of the broken bone and the rear end of the hollow outer sleeve lies adjacent the opposite outer surface of the broken bone such that said first wing can be rotated relative to said shaft such that its straight edge can move along one beveled edge on the front edge of the hollow outer sleeve and become aligned generally parallel to and adjacent the front edge of said hollow outer sleeve and lie along an adjacent section of outer bone surface to one side of said hollow outer sleeve and said second wing can be rotated relative to said shaft such that its straight edge can move along the opposite beveled edge on the front edge of the hollow outer sleeve and become aligned generally parallel to and adjacent the front edge of said hollow outer sleeve and lie along an adjacent section of outer bone surface to the opposite side of said hollow outer sleeve and said securing means is tightened against said rear end of said hollow outer sleeve to thereby provide a compressive force generated between said first and second rotatable wings and the securing means to thereby provide a compressive force to fixate the broken sections of bone together.

27. A winged compression bolt in accordance with claim 26 wherein said securing means further comprises a hollow collar having threads along a portion of its interior wall and fit around the rear end of said hollow outer sleeve, and a threaded bolt threaded into said hollow collar and press fit against said hollow sleeve such that said hollow collar can be rotated relative to the fixed bolt and tightened against the remote outer surface of the cortex of the bone.

28. A winged compression bolt in accordance with claim 26 wherein said elongated shaft further comprises a multiplicity of ridges on at least one of its lateral surfaces and said securing means further comprises a hollow collar having at least one tongue protruding inwardly whereby the hollow collar can be affixed to the elongated shaft by a mating of the at least one tongue with at least one ridge on the elongated shaft and the hollow collar is further press fit against the remote outer surface of the hollow sleeve.

29. A winged compression bolt in accordance with claim 26 wherein said elongated shaft further comprises a multiplicity of holes through its width and said securing means comprises a pin which can be placed through one of said holes in the elongated shaft and the pin is press fit against the outer hollow sleeve.

30. A winged compression bolt in accordance with claim 26 wherein a washer may be placed between said securing means and bone surface to create compression on the cortexes of bone.

31. A winged compression bolt for fixating broken sections of bone comprising:
 a. a hollow outer sleeve having a sidewall enclosing a centrally disposed opening within the sleeve, a front end and a rear end;
 b. an elongate shaft having a front end and a rear end and which is movably set in the opening in said hollow outer sleeve;
 c. at least one wing having a straight edge and rotatably supported via pivot means on said shaft front end;
 d. wherein said shaft front end and said pivot means extend beyond the front end of said hollow outer sleeve and said wing is rotatable into a deployed position to provide compressive force against the external surface of the cortex of a bone.

32. The invention in accordance with claim 31 wherein said hollow outer sleeve is moved against said wing causing it to rotate into the deployed position.

33. The invention in accordance with claim 31 further comprising means for providing a compressive force, said means comprising a pair of oppositely disposed wings each wing having a straight edge aligned against an edge of the hollow outer sleeve and against an adjacent surface of exterior bone when said wings are in the deployed position.

34. The invention in accordance with claim 31 further comprising
 a securing means on the rear end of the shaft which is tightened against the shaft and the exterior surface of the bone to create a compressive force between said wing and the securing means.

* * * * *